(12) United States Patent
Jeon et al.

(10) Patent No.: US 10,323,230 B2
(45) Date of Patent: Jun. 18, 2019

(54) METHOD FOR PREPARING A THREE-DIMENSIONALLY CULTURED SKIN COMPRISING DERMIS AND EPIDERMIS, AND THE CULTURED SKIN MADE THEREFROM

(71) Applicant: Saewha Jeon, Seoul (KR)

(72) Inventors: Saewha Jeon, Seoul (KR); Yun Hee Kim, Seoul (KR); Hyun Ah Moon, Incheon (KR)

(73) Assignee: Saewha Jeon, Seoul (KR)

( * ) Notice: Subject to any disclaimer, the term of this patent is extended or adjusted under 35 U.S.C. 154(b) by 0 days.

(21) Appl. No.: 15/324,277

(22) PCT Filed: Jul. 9, 2015

(86) PCT No.: PCT/KR2015/007118
§ 371 (c)(1),
(2) Date: Jan. 6, 2017

(87) PCT Pub. No.: WO2016/006944
PCT Pub. Date: Jan. 14, 2016

(65) Prior Publication Data
US 2017/0260511 A1  Sep. 14, 2017

(30) Foreign Application Priority Data
Jul. 9, 2014  (KR) .................. 10-2014-0086148

(51) Int. Cl.
| | |
|---|---|
| C12N 5/00 | (2006.01) |
| A61L 27/24 | (2006.01) |
| A61L 27/38 | (2006.01) |
| A61L 27/60 | (2006.01) |
| C12N 5/071 | (2010.01) |

(52) U.S. Cl.
CPC ............ *C12N 5/0698* (2013.01); *A61L 27/24* (2013.01); *A61L 27/38* (2013.01); *A61L 27/60* (2013.01); *C12N 5/0062* (2013.01); *C12N 5/0629* (2013.01); *C12N 2502/1323* (2013.01); *C12N 2533/54* (2013.01)

(58) Field of Classification Search
CPC .......................... C12N 5/0698; C12N 5/0062; C12N 5/0629; C12N 2533/54; C12N 2502/1323; A61L 27/24; A61L 27/60; A61L 27/38
See application file for complete search history.

(56) References Cited

U.S. PATENT DOCUMENTS

2003/0109920 A1  6/2003  Martins-Green et al.

FOREIGN PATENT DOCUMENTS

| | | |
|---|---|---|
| EP | 1930411 A1 | 11/2008 |
| JP | 06-292568 A | 2/1994 |
| JP | 09-173362 A | 7/1997 |
| JP | 2012-235921 A | 12/2012 |
| KR | 10-0818636 B1 | 4/2008 |
| KR | 10-2013-0056956 A | 5/2013 |
| WO | 2006088029 A1 | 8/2006 |

OTHER PUBLICATIONS

Carlson et al., Current Protocols in Cell Biology 19.9.1-19.9.17, Supplement 41, Dec. 2008, John Wiley & Sons, Inc., published online Dec. 2008 in Wiley Interscience.*
Ikuta et al., Biosci. Biotechnol. Biochem., 2006, vol. 70, No. 11, p. 2669-2675.*
Ono et al., J Biomed Mater Res, 1999, vol. 48, p. 621-630.*
Archambault et al., J Invest. Dermatol., 1995, vol. 104, p. 859-867.*
Koken AteloCell, Mar. 8, 2011, 3 pages of PDF.*
Amano, Saroshi et al. "Importance of Balance between Extracellular Matrix Synthesis and Degradation in Basement Membrane Formation" Experimental Cell Research, 2001, vol. 271, 249-262.
Extended European Search Report EP 15819565.1 dated Feb. 5, 2018.
The Japanese Journal of Dermatology, 1987, vol. 97, No. 11, pp. 1247-1251.
Office Action JP 2017-501265 dated Jan. 9, 2018.
Wilson, Jeffrey L. et al. "Epithelial-specific Gene Expression during Differentiation of Stratified Primary Human Keratinocyte Cultures" Cell Growth & Differentiation, 1992, vol. 3, pp. 471-483.
Yang, Eun-Kyoung et al. "Development of Dermal Equivalent Using Mouse Fibroblasts" Korean Journal of Applied Mecrobiology and Biotechnology, 1993, vol. 21, No. 4, pp. 381-391.

* cited by examiner

*Primary Examiner* — Kade Ariani
(74) *Attorney, Agent, or Firm* — Edwin S. Flores; Daniel J. Chalker; Chalker Flores, LLP

(57) ABSTRACT

The present invention includes a method for preparing a three-dimensionally cultured skin model comprising dermis and epidermis, which comprises: a step of preparing the dermis using a composition comprising murine fibroblasts; and a combination of native collagen and atelocollagen; and a step of forming the epidermis using keratinocytes. Also, the present invention relates to a three-dimensionally cultured skin model which comprises: a dermis prepared by a composition comprising murine fibroblasts, native collagen, or a combination of native collagen and atelocollagen; and epidermis formed from keratinocytes.

10 Claims, 7 Drawing Sheets
Specification includes a Sequence Listing.

E) epidermis, D) dermis

Atello:Native
(1:1)

Atello:Native
(1:5)

Atello:Native
(1:10)

SEQUENCE LISTING

```
<160> NUMBER OF SEQ ID NOS: 4

<210> SEQ ID NO 1
<211> LENGTH: 1364
<212> TYPE: PRT
<213> ORGANISM: Bos taurus

<400> SEQUENCE: 1

Met Leu Ser Phe Val Asp Thr Arg Thr Leu Leu Leu Leu Ala Val Thr
1               5                   10                  15

Ser Cys Leu Ala Thr Cys Gln Ser Leu Gln Glu Ala Thr Ala Arg Lys
            20                  25                  30

Gly Pro Ser Gly Asp Arg Gly Pro Arg Gly Glu Arg Gly Pro Pro Gly
        35                  40                  45

Pro Pro Gly Arg Asp Gly Asp Asp Gly Ile Pro Gly Pro Pro Gly Pro
    50                  55                  60

Pro Gly Pro Pro Gly Pro Pro Gly Leu Gly Gly Asn Phe Ala Ala Gln
65                  70                  75                  80
```

```
Phe Asp Ala Lys Gly Gly Pro Gly Pro Met Gly Leu Met Gly Pro
                85                  90                  95
Arg Gly Pro Pro Gly Ala Ser Gly Ala Pro Gly Pro Gln Gly Phe Gln
            100                 105                 110
Gly Pro Pro Gly Glu Pro Gly Glu Pro Gly Gln Thr Gly Pro Ala Gly
        115                 120                 125
Ala Arg Gly Pro Pro Gly Pro Pro Gly Lys Ala Gly Glu Asp Gly His
130                 135                 140
Pro Gly Lys Pro Gly Arg Pro Gly Glu Arg Gly Val Val Gly Pro Gln
145                 150                 155                 160
Gly Ala Arg Gly Phe Pro Gly Thr Pro Gly Leu Pro Gly Phe Lys Gly
                165                 170                 175
Ile Arg Gly His Asn Gly Leu Asp Gly Leu Lys Gly Gln Pro Gly Ala
            180                 185                 190
Pro Gly Val Lys Gly Glu Pro Gly Ala Pro Gly Glu Asn Gly Thr Pro
        195                 200                 205
Gly Gln Thr Gly Ala Arg Gly Leu Pro Gly Glu Arg Gly Arg Val Gly
    210                 215                 220
Ala Pro Gly Pro Ala Gly Ala Arg Gly Ser Asp Gly Ser Val Gly Pro
225                 230                 235                 240
Val Gly Pro Ala Gly Pro Ile Gly Ser Ala Gly Pro Pro Gly Phe Pro
                245                 250                 255
Gly Ala Pro Gly Pro Lys Gly Glu Leu Gly Pro Val Gly Asn Pro Gly
            260                 265                 270
Pro Ala Gly Pro Ala Gly Pro Arg Gly Glu Val Gly Leu Pro Gly Leu
        275                 280                 285
Ser Gly Pro Val Gly Pro Pro Gly Asn Pro Gly Ala Asn Gly Leu Pro
    290                 295                 300
Gly Ala Lys Gly Ala Ala Gly Leu Pro Gly Val Ala Gly Ala Pro Gly
305                 310                 315                 320
Leu Pro Gly Pro Arg Gly Ile Pro Gly Pro Val Gly Ala Ala Gly Ala
                325                 330                 335
Thr Gly Ala Arg Gly Leu Val Gly Glu Pro Gly Pro Ala Gly Ser Lys
            340                 345                 350
Gly Glu Ser Gly Asn Lys Gly Glu Pro Gly Ala Val Gly Gln Pro Gly
        355                 360                 365
Pro Pro Gly Pro Ser Gly Glu Glu Gly Lys Arg Gly Ser Thr Gly Glu
    370                 375                 380
Ile Gly Pro Ala Gly Pro Pro Gly Pro Pro Gly Leu Arg Gly Asn Pro
385                 390                 395                 400
Gly Ser Arg Gly Leu Pro Gly Ala Asp Gly Arg Ala Gly Val Met Gly
                405                 410                 415
Pro Ala Gly Ser Arg Gly Ala Thr Gly Pro Ala Gly Val Arg Gly Pro
            420                 425                 430
Asn Gly Asp Ser Gly Arg Pro Gly Glu Pro Gly Leu Met Gly Pro Arg
        435                 440                 445
Gly Phe Pro Gly Ser Pro Gly Asn Ile Gly Pro Ala Gly Lys Glu Gly
    450                 455                 460
Pro Val Gly Leu Pro Gly Ile Asp Gly Arg Pro Gly Pro Ile Gly Pro
465                 470                 475                 480
Ala Gly Ala Arg Gly Glu Pro Gly Asn Ile Gly Phe Pro Gly Pro Lys
                485                 490                 495
```

```
Gly Pro Ser Gly Asp Pro Gly Lys Ala Gly Lys Gly His Ala Gly
            500                 505                 510
Leu Ala Gly Ala Arg Gly Ala Pro Gly Pro Asp Gly Asn Asn Gly Ala
        515                 520                 525
Gln Gly Pro Pro Gly Leu Gln Gly Val Gln Gly Gly Lys Gly Glu Gln
        530                 535                 540
Gly Pro Ala Gly Pro Pro Gly Phe Gln Gly Leu Pro Gly Pro Ala Gly
545                 550                 555                 560
Thr Ala Gly Glu Ala Gly Lys Pro Gly Glu Arg Gly Ile Pro Gly Glu
            565                 570                 575
Phe Gly Leu Pro Gly Pro Ala Gly Ala Arg Gly Glu Arg Gly Pro Pro
        580                 585                 590
Gly Glu Ser Gly Ala Ala Gly Pro Thr Gly Pro Ile Gly Ser Arg Gly
        595                 600                 605
Pro Ser Gly Pro Pro Gly Pro Asp Gly Asn Lys Gly Glu Pro Gly Val
        610                 615                 620
Val Gly Ala Pro Gly Thr Ala Gly Pro Ser Gly Pro Ser Gly Leu Pro
625                 630                 635                 640
Gly Glu Arg Gly Ala Ala Gly Ile Pro Gly Gly Lys Gly Glu Lys Gly
            645                 650                 655
Glu Thr Gly Leu Arg Gly Asp Ile Gly Ser Pro Gly Arg Asp Gly Ala
            660                 665                 670
Arg Gly Ala Pro Gly Ala Ile Gly Ala Pro Gly Pro Ala Gly Ala Asn
        675                 680                 685
Gly Asp Arg Gly Glu Ala Gly Pro Ala Gly Pro Ala Gly Pro Ala Gly
        690                 695                 700
Pro Arg Gly Ser Pro Gly Glu Arg Gly Glu Val Gly Pro Ala Gly Pro
705                 710                 715                 720
Asn Gly Phe Ala Gly Pro Ala Gly Ala Ala Gly Gln Pro Gly Ala Lys
            725                 730                 735
Gly Glu Arg Gly Thr Lys Gly Pro Lys Gly Glu Asn Gly Pro Val Gly
            740                 745                 750
Pro Thr Gly Pro Val Gly Ala Ala Gly Pro Ser Gly Pro Asn Gly Pro
        755                 760                 765
Pro Gly Pro Ala Gly Ser Arg Gly Asp Gly Gly Pro Pro Gly Ala Thr
        770                 775                 780
Gly Phe Pro Gly Ala Ala Gly Arg Thr Gly Pro Pro Gly Pro Ser Gly
785                 790                 795                 800
Ile Ser Gly Pro Pro Gly Pro Pro Gly Pro Ala Gly Lys Glu Gly Leu
            805                 810                 815
Arg Gly Pro Arg Gly Asp Gln Gly Pro Val Gly Arg Ser Gly Glu Thr
            820                 825                 830
Gly Ala Ser Gly Pro Pro Gly Phe Val Gly Glu Lys Gly Pro Ser Gly
        835                 840                 845
Glu Pro Gly Thr Ala Gly Pro Pro Gly Thr Pro Gly Pro Gln Gly Leu
        850                 855                 860
Leu Gly Ala Pro Gly Phe Leu Gly Leu Pro Gly Ser Arg Gly Glu Arg
865                 870                 875                 880
Gly Leu Pro Gly Val Ala Gly Ser Val Gly Glu Pro Gly Pro Leu Gly
            885                 890                 895
Ile Ala Gly Pro Pro Gly Ala Arg Gly Pro Pro Gly Asn Val Gly Asn
            900                 905                 910
Pro Gly Val Asn Gly Ala Pro Gly Glu Ala Gly Arg Asp Gly Asn Pro
```

```
                915                 920                 925
Gly Asn Asp Gly Pro Pro Gly Arg Asp Gly Gln Pro Gly His Lys Gly
    930                 935                 940
Glu Arg Gly Tyr Pro Gly Asn Ala Gly Pro Val Gly Ala Ala Gly Ala
945                 950                 955                 960
Pro Gly Pro Gln Gly Pro Val Gly Pro Val Gly Lys His Gly Asn Arg
                965                 970                 975
Gly Glu Pro Gly Pro Ala Gly Ala Val Gly Pro Ala Gly Ala Val Gly
            980                 985                 990
Pro Arg Gly Pro Ser Gly Pro Gln Gly Ile Arg Gly Asp Lys Gly Glu
                995                1000                1005
Pro Gly Asp Lys Gly Pro Arg Gly Leu Pro Gly Leu Lys Gly His
   1010                1015                1020
Asn Gly Leu Gln Gly Leu Pro Gly Leu Ala Gly His His Gly Asp
   1025                1030                1035
Gln Gly Ala Pro Gly Ala Val Gly Pro Ala Gly Pro Arg Gly Pro
   1040                1045                1050
Ala Gly Pro Ser Gly Pro Ala Gly Lys Asp Gly Arg Ile Gly Gln
   1055                1060                1065
Pro Gly Ala Val Gly Pro Ala Gly Ile Arg Gly Ser Gln Gly Ser
   1070                1075                1080
Gln Gly Pro Ala Gly Pro Pro Gly Pro Pro Gly Pro Pro Gly Pro
   1085                1090                1095
Pro Gly Pro Ser Gly Gly Gly Tyr Glu Phe Gly Phe Asp Gly Asp
   1100                1105                1110
Phe Tyr Arg Ala Asp Gln Pro Arg Ser Pro Thr Ser Leu Arg Pro
   1115                1120                1125
Lys Asp Tyr Glu Val Asp Ala Thr Leu Lys Ser Leu Asn Asn Gln
   1130                1135                1140
Ile Glu Thr Leu Leu Thr Pro Glu Gly Ser Arg Lys Asn Pro Ala
   1145                1150                1155
Arg Thr Cys Arg Asp Leu Arg Leu Ser His Pro Glu Trp Ser Ser
   1160                1165                1170
Gly Tyr Tyr Trp Ile Asp Pro Asn Gln Gly Cys Thr Met Asp Ala
   1175                1180                1185
Ile Lys Val Tyr Cys Asp Phe Ser Thr Gly Glu Thr Cys Ile Arg
   1190                1195                1200
Ala Gln Pro Glu Asp Ile Pro Val Lys Asn Trp Tyr Arg Asn Ser
   1205                1210                1215
Lys Ala Lys Lys His Val Trp Val Gly Glu Thr Ile Asn Gly Gly
   1220                1225                1230
Thr Gln Phe Glu Tyr Asn Val Glu Gly Val Thr Thr Lys Glu Met
   1235                1240                1245
Ala Thr Gln Leu Ala Phe Met Arg Leu Leu Ala Asn His Ala Ser
   1250                1255                1260
Gln Asn Ile Thr Tyr His Cys Lys Asn Ser Ile Ala Tyr Met Asp
   1265                1270                1275
Glu Glu Thr Gly Asn Leu Lys Lys Ala Val Ile Leu Gln Gly Ser
   1280                1285                1290
Asn Asp Val Glu Leu Val Ala Glu Gly Asn Ser Arg Phe Thr Tyr
   1295                1300                1305
Thr Val Leu Val Asp Gly Cys Ser Lys Lys Thr Asn Glu Trp Gln
   1310                1315                1320
```

```
Lys Thr Ile Ile Glu Tyr Lys Thr Asn Lys Pro Ser Arg Leu Pro
    1325                1330                1335

Ile Leu Asp Ile Ala Pro Leu Asp Ile Gly Gly Ala Asp Gln Glu
    1340                1345                1350

Ile Arg Leu Asn Ile Gly Pro Val Cys Phe Lys
    1355                1360

<210> SEQ ID NO 2
<211> LENGTH: 1364
<212> TYPE: PRT
<213> ORGANISM: Bos taurus

<400> SEQUENCE: 2

Met Leu Ser Phe Val Asp Thr Arg Thr Leu Leu Leu Ala Val Thr
1               5                   10                  15

Ser Cys Leu Ala Thr Cys Gln Ser Leu Gln Glu Ala Thr Ala Arg Lys
                20                  25                  30

Gly Pro Ser Gly Asp Arg Gly Pro Arg Gly Glu Arg Gly Pro Pro Gly
                35                  40                  45

Pro Pro Gly Arg Asp Gly Asp Asp Gly Ile Pro Gly Pro Pro Gly Pro
50                      55                  60

Pro Gly Pro Pro Gly Pro Gly Leu Gly Gly Asn Phe Ala Ala Gln
65                      70                  75                  80

Phe Asp Ala Lys Gly Gly Gly Pro Gly Pro Met Gly Leu Met Gly Pro
                85                  90                  95

Arg Gly Pro Pro Gly Ala Ser Gly Ala Pro Gly Pro Gln Gly Phe Gln
                100                 105                 110

Gly Pro Pro Gly Glu Pro Gly Glu Pro Gly Gln Thr Gly Pro Ala Gly
                115                 120                 125

Ala Arg Gly Pro Pro Gly Pro Pro Gly Lys Ala Gly Glu Asp Gly His
                130                 135                 140

Pro Gly Lys Pro Gly Arg Pro Gly Glu Arg Gly Val Val Gly Pro Gln
145                     150                 155                 160

Gly Ala Arg Gly Phe Pro Gly Thr Pro Gly Leu Pro Gly Phe Lys Gly
                165                 170                 175

Ile Arg Gly His Asn Gly Leu Asp Gly Leu Lys Gly Gln Pro Gly Ala
                180                 185                 190

Pro Gly Val Lys Gly Glu Pro Gly Ala Pro Gly Glu Asn Gly Thr Pro
                195                 200                 205

Gly Gln Thr Gly Ala Arg Gly Leu Pro Gly Glu Arg Gly Arg Val Gly
                210                 215                 220

Ala Pro Gly Pro Ala Gly Ala Arg Gly Ser Asp Gly Ser Val Gly Pro
225                     230                 235                 240

Val Gly Pro Ala Gly Pro Ile Gly Ser Ala Gly Pro Pro Gly Phe Pro
                245                 250                 255

Gly Ala Pro Gly Pro Lys Gly Glu Leu Gly Pro Val Gly Asn Pro Gly
                260                 265                 270

Pro Ala Gly Pro Ala Gly Pro Arg Gly Glu Val Gly Leu Pro Gly Leu
                275                 280                 285

Ser Gly Pro Val Gly Pro Pro Gly Asn Pro Gly Ala Asn Gly Leu Pro
                290                 295                 300

Gly Ala Lys Gly Ala Ala Gly Leu Pro Gly Val Ala Gly Ala Pro Gly
305                     310                 315                 320

Leu Pro Gly Pro Arg Gly Ile Pro Gly Pro Val Gly Ala Ala Gly Ala
```

```
            325                 330                 335
Thr Gly Ala Arg Gly Leu Val Gly Glu Pro Gly Pro Ala Gly Ser Lys
            340                 345                 350
Gly Glu Ser Gly Asn Lys Gly Glu Pro Gly Ala Val Gly Gln Pro Gly
            355                 360                 365
Pro Pro Gly Pro Ser Gly Glu Gly Lys Arg Gly Ser Thr Gly Glu
            370                 375                 380
Ile Gly Pro Ala Gly Pro Gly Pro Pro Gly Leu Arg Gly Asn Pro
385                 390                 395                 400
Gly Ser Arg Gly Leu Pro Gly Ala Asp Gly Arg Ala Gly Val Met Gly
            405                 410                 415
Pro Ala Gly Ser Arg Gly Ala Thr Gly Pro Ala Gly Val Arg Gly Pro
            420                 425                 430
Asn Gly Asp Ser Gly Arg Pro Gly Glu Pro Gly Leu Met Gly Pro Arg
            435                 440                 445
Gly Phe Pro Gly Ser Pro Gly Asn Ile Gly Pro Ala Gly Lys Glu Gly
            450                 455                 460
Pro Val Gly Leu Pro Gly Ile Asp Gly Arg Pro Gly Pro Ile Gly Pro
465                 470                 475                 480
Ala Gly Ala Arg Gly Glu Pro Gly Asn Ile Gly Phe Pro Gly Pro Lys
            485                 490                 495
Gly Pro Ser Gly Asp Pro Gly Lys Ala Gly Glu Lys Gly His Ala Gly
            500                 505                 510
Leu Ala Gly Ala Arg Gly Ala Pro Gly Pro Asp Gly Asn Asn Gly Ala
            515                 520                 525
Gln Gly Pro Pro Gly Leu Gln Gly Val Gln Gly Gly Lys Gly Glu Gln
            530                 535                 540
Gly Pro Ala Gly Pro Pro Gly Phe Gln Gly Leu Pro Gly Pro Ala Gly
545                 550                 555                 560
Thr Ala Gly Glu Ala Gly Lys Pro Gly Glu Arg Gly Ile Pro Gly Glu
            565                 570                 575
Phe Gly Leu Pro Gly Pro Ala Gly Ala Arg Gly Glu Arg Gly Pro Pro
            580                 585                 590
Gly Glu Ser Gly Ala Ala Gly Pro Thr Gly Pro Ile Gly Ser Arg Gly
            595                 600                 605
Pro Ser Gly Pro Pro Gly Pro Asp Gly Asn Lys Gly Glu Pro Gly Val
            610                 615                 620
Val Gly Ala Pro Gly Thr Ala Gly Pro Ser Gly Pro Ser Gly Leu Pro
625                 630                 635                 640
Gly Glu Arg Gly Ala Ala Gly Ile Pro Gly Gly Lys Gly Glu Lys Gly
            645                 650                 655
Glu Thr Gly Leu Arg Gly Asp Ile Gly Ser Pro Gly Arg Asp Gly Ala
            660                 665                 670
Arg Gly Ala Pro Gly Ala Ile Gly Ala Pro Gly Pro Ala Gly Ala Asn
            675                 680                 685
Gly Asp Arg Gly Glu Ala Gly Pro Ala Gly Pro Ala Gly Pro Ala Gly
            690                 695                 700
Pro Arg Gly Ser Pro Gly Glu Arg Gly Glu Val Gly Pro Ala Gly Pro
705                 710                 715                 720
Asn Gly Phe Ala Gly Pro Ala Gly Ala Ala Gly Gln Pro Gly Ala Lys
            725                 730                 735
Gly Glu Arg Gly Thr Lys Gly Pro Lys Gly Glu Asn Gly Pro Val Gly
            740                 745                 750
```

```
Pro Thr Gly Pro Val Gly Ala Ala Gly Pro Ser Gly Pro Asn Gly Pro
        755                 760                 765
Pro Gly Pro Ala Gly Ser Arg Gly Asp Gly Pro Pro Gly Ala Thr
        770                 775                 780
Gly Phe Pro Gly Ala Ala Gly Arg Thr Gly Pro Pro Gly Pro Ser Gly
785                 790                 795                 800
Ile Ser Gly Pro Pro Gly Pro Pro Gly Pro Ala Gly Lys Glu Gly Leu
                805                 810                 815
Arg Gly Pro Arg Gly Asp Gln Gly Pro Val Gly Arg Ser Gly Glu Thr
                820                 825                 830
Gly Ala Ser Gly Pro Pro Gly Phe Val Gly Glu Lys Gly Pro Ser Gly
                835                 840                 845
Glu Pro Gly Thr Ala Gly Pro Pro Gly Thr Pro Gly Pro Gln Gly Leu
                850                 855                 860
Leu Gly Ala Pro Gly Phe Leu Gly Leu Pro Gly Ser Arg Gly Glu Arg
865                 870                 875                 880
Gly Leu Pro Gly Val Ala Gly Ser Val Gly Glu Pro Gly Pro Leu Gly
                        885                 890                 895
Ile Ala Gly Pro Pro Gly Ala Arg Gly Pro Pro Gly Asn Val Gly Asn
                900                 905                 910
Pro Gly Val Asn Gly Ala Pro Gly Glu Ala Gly Arg Asp Gly Asn Pro
                915                 920                 925
Gly Asn Asp Gly Pro Pro Gly Arg Asp Gly Gln Pro Gly His Lys Gly
                930                 935                 940
Glu Arg Gly Tyr Pro Gly Asn Ala Gly Pro Val Gly Ala Ala Gly Ala
945                 950                 955                 960
Pro Gly Pro Gln Gly Pro Val Gly Pro Val Gly Lys His Gly Asn Arg
                965                 970                 975
Gly Glu Pro Gly Pro Ala Gly Ala Val Gly Pro Ala Gly Ala Val Gly
                980                 985                 990
Pro Arg Gly Pro Ser Gly Pro Gln Gly Ile Arg Gly Asp Lys Gly Glu
                995                 1000                1005
Pro Gly Asp Lys Gly Pro Arg Gly Leu Pro Gly Leu Lys Gly His
        1010                1015                1020
Asn Gly Leu Gln Gly Leu Pro Gly Leu Ala Gly His His Gly Asp
        1025                1030                1035
Gln Gly Ala Pro Gly Ala Val Gly Pro Ala Gly Pro Arg Gly Pro
        1040                1045                1050
Ala Gly Pro Ser Gly Pro Ala Gly Lys Asp Gly Arg Ile Gly Gln
        1055                1060                1065
Pro Gly Ala Val Gly Pro Ala Gly Ile Arg Gly Ser Gln Gly Ser
        1070                1075                1080
Gln Gly Pro Ala Gly Pro Pro Gly Pro Pro Gly Pro Pro Gly Pro
        1085                1090                1095
Pro Gly Pro Ser Gly Gly Gly Tyr Glu Phe Gly Phe Asp Gly Asp
        1100                1105                1110
Phe Tyr Arg Ala Asp Gln Pro Arg Ser Pro Thr Ser Leu Arg Pro
        1115                1120                1125
Lys Asp Tyr Glu Val Asp Ala Thr Leu Lys Ser Leu Asn Asn Gln
        1130                1135                1140
Ile Glu Thr Leu Leu Thr Pro Glu Gly Ser Arg Lys Asn Pro Ala
        1145                1150                1155
```

-continued

```
Arg Thr Cys Arg Asp Leu Arg Leu Ser His Pro Glu Trp Ser Ser
    1160                1165                1170

Gly Tyr Tyr Trp Ile Asp Pro Asn Gln Gly Cys Thr Met Asp Ala
    1175                1180                1185

Ile Lys Val Tyr Cys Asp Phe Ser Thr Gly Glu Thr Cys Ile Arg
    1190                1195                1200

Ala Gln Pro Glu Asp Ile Pro Val Lys Asn Trp Tyr Arg Asn Ser
    1205                1210                1215

Lys Ala Lys Lys His Val Trp Val Gly Glu Thr Ile Asn Gly Gly
    1220                1225                1230

Thr Gln Phe Glu Tyr Asn Val Glu Gly Val Thr Thr Lys Glu Met
    1235                1240                1245

Ala Thr Gln Leu Ala Phe Met Arg Leu Leu Ala Asn His Ala Ser
    1250                1255                1260

Gln Asn Ile Thr Tyr His Cys Lys Asn Ser Ile Ala Tyr Met Asp
    1265                1270                1275

Glu Glu Thr Gly Asn Leu Lys Lys Ala Val Ile Leu Gln Gly Ser
    1280                1285                1290

Asn Asp Val Glu Leu Val Ala Glu Gly Asn Ser Arg Phe Thr Tyr
    1295                1300                1305

Thr Val Leu Val Asp Gly Cys Ser Lys Lys Thr Asn Glu Trp Gln
    1310                1315                1320

Lys Thr Ile Ile Glu Tyr Lys Thr Asn Lys Pro Ser Arg Leu Pro
    1325                1330                1335

Ile Leu Asp Ile Ala Pro Leu Asp Ile Gly Gly Ala Asp Gln Glu
    1340                1345                1350

Ile Arg Leu Asn Ile Gly Pro Val Cys Phe Lys
    1355                1360

<210> SEQ ID NO 3
<211> LENGTH: 1014
<212> TYPE: PRT
<213> ORGANISM: Bos taurus

<400> SEQUENCE: 3

Arg Gly His Asn Gly Leu Asp Gly Leu Lys Gly Gln Pro Gly Ala Pro
1               5                   10                  15

Gly Val Lys Gly Glu Pro Gly Ala Pro Gly Glu Asn Gly Thr Pro Gly
                20                  25                  30

Gln Thr Gly Ala Arg Gly Leu Pro Gly Glu Arg Gly Arg Val Gly Ala
        35                  40                  45

Pro Gly Pro Ala Gly Ala Arg Gly Ser Asp Gly Ser Val Gly Pro Val
    50                  55                  60

Gly Pro Ala Gly Pro Ile Gly Ser Ala Gly Pro Gly Phe Pro Gly
65                  70                  75                  80

Ala Pro Gly Pro Lys Gly Glu Leu Gly Pro Val Gly Asn Pro Gly Pro
                85                  90                  95

Ala Gly Pro Ala Gly Pro Arg Gly Glu Val Gly Leu Pro Gly Leu Ser
            100                 105                 110

Gly Pro Val Gly Pro Gly Asn Pro Gly Ala Asn Gly Leu Pro Gly
        115                 120                 125

Ala Lys Gly Ala Ala Gly Leu Pro Gly Val Gly Ala Pro Gly Leu
    130                 135                 140

Pro Gly Pro Arg Gly Ile Pro Gly Pro Val Gly Ala Ala Gly Ala Thr
145                 150                 155                 160
```

```
Gly Ala Arg Gly Leu Val Gly Glu Pro Gly Pro Ala Gly Ser Lys Gly
                165                 170                 175

Glu Ser Gly Asn Lys Gly Glu Pro Gly Ala Val Gly Gln Pro Gly Pro
            180                 185                 190

Pro Gly Pro Ser Gly Glu Glu Gly Lys Arg Gly Ser Thr Gly Glu Ile
        195                 200                 205

Gly Pro Ala Gly Pro Pro Gly Pro Pro Gly Leu Arg Gly Asn Pro Gly
    210                 215                 220

Ser Arg Gly Leu Pro Gly Ala Asp Gly Arg Ala Gly Val Met Gly Pro
225                 230                 235                 240

Ala Gly Ser Arg Gly Ala Thr Gly Pro Ala Gly Val Arg Gly Pro Asn
                245                 250                 255

Gly Asp Ser Gly Arg Pro Gly Glu Pro Gly Leu Met Gly Pro Arg Gly
            260                 265                 270

Phe Pro Gly Ser Pro Gly Asn Ile Gly Pro Ala Gly Lys Glu Gly Pro
        275                 280                 285

Val Gly Leu Pro Gly Ile Asp Gly Arg Pro Gly Pro Ile Gly Pro Ala
    290                 295                 300

Gly Ala Arg Gly Glu Pro Gly Asn Ile Gly Phe Pro Gly Pro Lys Gly
305                 310                 315                 320

Pro Ser Gly Asp Pro Gly Lys Ala Gly Glu Lys Gly His Ala Gly Leu
                325                 330                 335

Ala Gly Ala Arg Gly Ala Pro Gly Pro Asp Gly Asn Asn Gly Ala Gln
            340                 345                 350

Gly Pro Pro Gly Leu Gln Gly Val Gln Gly Gly Lys Gly Glu Gln Gly
        355                 360                 365

Pro Ala Gly Pro Pro Gly Phe Gln Gly Leu Pro Gly Pro Ala Gly Thr
    370                 375                 380

Ala Gly Glu Ala Gly Lys Pro Gly Glu Arg Gly Ile Pro Gly Glu Phe
385                 390                 395                 400

Gly Leu Pro Gly Pro Ala Gly Ala Arg Gly Glu Arg Gly Pro Pro Gly
                405                 410                 415

Glu Ser Gly Ala Ala Gly Pro Thr Gly Pro Ile Gly Ser Arg Gly Pro
            420                 425                 430

Ser Gly Pro Pro Gly Pro Asp Gly Asn Lys Gly Glu Pro Gly Val Val
        435                 440                 445

Gly Ala Pro Gly Thr Ala Gly Pro Ser Gly Pro Ser Gly Leu Pro Gly
    450                 455                 460

Glu Arg Gly Ala Ala Gly Ile Pro Gly Gly Lys Gly Glu Lys Gly Glu
465                 470                 475                 480

Thr Gly Leu Arg Gly Asp Ile Gly Ser Pro Gly Arg Asp Gly Ala Arg
                485                 490                 495

Gly Ala Pro Gly Ala Ile Gly Ala Pro Gly Pro Ala Gly Ala Asn Gly
            500                 505                 510

Asp Arg Gly Glu Ala Gly Pro Ala Gly Pro Ala Gly Pro Ala Gly Pro
        515                 520                 525

Arg Gly Ser Pro Gly Glu Arg Gly Glu Val Gly Pro Ala Gly Pro Asn
    530                 535                 540

Gly Phe Ala Gly Pro Ala Gly Ala Ala Gly Gln Pro Gly Ala Lys Gly
545                 550                 555                 560

Glu Arg Gly Thr Lys Gly Pro Lys Gly Glu Asn Gly Pro Val Gly Pro
                565                 570                 575
```

```
Thr Gly Pro Val Gly Ala Ala Gly Pro Ser Gly Pro Asn Gly Pro Pro
            580                 585                 590

Gly Pro Ala Gly Ser Arg Gly Asp Gly Gly Pro Gly Ala Thr Gly
        595                 600                 605

Phe Pro Gly Ala Ala Gly Arg Thr Gly Pro Pro Gly Pro Ser Gly Ile
            610                 615                 620

Ser Gly Pro Pro Gly Pro Pro Gly Pro Ala Gly Lys Glu Gly Leu Arg
625                 630                 635                 640

Gly Pro Arg Gly Asp Gln Gly Pro Val Gly Arg Ser Gly Glu Thr Gly
                645                 650                 655

Ala Ser Gly Pro Pro Gly Phe Val Gly Glu Lys Gly Pro Ser Gly Glu
            660                 665                 670

Pro Gly Thr Ala Gly Pro Pro Gly Thr Pro Gly Pro Gln Gly Leu Leu
            675                 680                 685

Gly Ala Pro Gly Phe Leu Gly Leu Pro Gly Ser Arg Gly Glu Arg Gly
            690                 695                 700

Leu Pro Gly Val Ala Gly Ser Val Gly Glu Pro Gly Pro Leu Gly Ile
705                 710                 715                 720

Ala Gly Pro Pro Gly Ala Arg Gly Pro Pro Gly Asn Val Gly Asn Pro
            725                 730                 735

Gly Val Asn Gly Ala Pro Gly Glu Ala Gly Arg Asp Gly Asn Pro Gly
            740                 745                 750

Asn Asp Gly Pro Pro Gly Arg Asp Gly Gln Pro Gly His Lys Gly Glu
            755                 760                 765

Arg Gly Tyr Pro Gly Asn Ala Gly Pro Val Gly Ala Ala Gly Ala Pro
            770                 775                 780

Gly Pro Gln Gly Pro Val Gly Pro Val Gly Lys His Gly Asn Arg Gly
785                 790                 795                 800

Glu Pro Gly Pro Ala Gly Ala Val Gly Pro Ala Gly Ala Val Gly Pro
                805                 810                 815

Arg Gly Pro Ser Gly Pro Gln Gly Ile Arg Gly Asp Lys Gly Glu Pro
            820                 825                 830

Gly Asp Lys Gly Pro Arg Gly Leu Pro Gly Leu Lys Gly His Asn Gly
            835                 840                 845

Leu Gln Gly Leu Pro Gly Leu Ala Gly His His Gly Asp Gln Gly Ala
            850                 855                 860

Pro Gly Ala Val Gly Pro Ala Gly Pro Arg Gly Pro Ala Gly Pro Ser
865                 870                 875                 880

Gly Pro Ala Gly Lys Asp Gly Arg Ile Gly Gln Pro Gly Ala Val Gly
                885                 890                 895

Pro Ala Gly Ile Arg Gly Ser Gln Gly Ser Gln Gly Pro Ala Gly Pro
            900                 905                 910

Pro Gly Pro Pro Gly Pro Pro Gly Pro Pro Gly Pro Ser Gly Gly Gly
            915                 920                 925

Tyr Glu Phe Gly Phe Asp Gly Asp Phe Tyr Arg Ala Asp Gln Pro Arg
            930                 935                 940

Ser Pro Thr Ser Leu Arg Pro Lys Asp Tyr Glu Val Asp Ala Thr Leu
945                 950                 955                 960

Lys Ser Leu Asn Asn Gln Ile Glu Thr Leu Leu Thr Pro Glu Gly Ser
                965                 970                 975

Arg Lys Asn Pro Ala Arg Thr Cys Arg Asp Leu Arg Leu Ser His Pro
            980                 985                 990

Glu Trp Ser Ser Gly Tyr Tyr Trp Ile Asp Pro Asn Gln Gly Cys Thr
```

```
                    995              1000              1005

Met Asp Ala Ile Lys Val
        1010

<210> SEQ ID NO 4
<211> LENGTH: 970
<212> TYPE: PRT
<213> ORGANISM: Bos taurus

<400> SEQUENCE: 4

Gln Gly Ala Arg Gly Phe Pro Gly Thr Pro Gly Leu Pro Gly Phe Lys
1               5                   10                  15

Gly Ile Arg Gly His Asn Gly Leu Asp Gly Leu Lys Gly Gln Pro Gly
            20                  25                  30

Ala Pro Gly Val Lys Gly Glu Pro Gly Ala Pro Gly Glu Asn Gly Thr
        35                  40                  45

Pro Gly Gln Thr Gly Ala Arg Gly Leu Pro Gly Glu Arg Gly Arg Val
    50                  55                  60

Gly Ala Pro Gly Pro Ala Gly Ala Arg Gly Ser Asp Gly Ser Val Gly
65                  70                  75                  80

Pro Val Gly Pro Ala Gly Pro Ile Gly Ser Ala Gly Pro Pro Gly Phe
                85                  90                  95

Pro Gly Ala Pro Gly Pro Lys Gly Glu Leu Gly Pro Val Gly Asn Pro
            100                 105                 110

Gly Pro Ala Gly Pro Ala Gly Pro Arg Gly Glu Val Gly Leu Pro Gly
        115                 120                 125

Leu Ser Gly Pro Val Gly Pro Pro Gly Asn Pro Gly Ala Asn Gly Leu
    130                 135                 140

Pro Gly Ala Lys Gly Ala Ala Gly Leu Pro Gly Val Ala Gly Ala Pro
145                 150                 155                 160

Gly Leu Pro Gly Pro Arg Gly Ile Pro Gly Pro Val Gly Ala Ala Gly
                165                 170                 175

Ala Thr Gly Ala Arg Gly Leu Val Gly Glu Pro Gly Pro Ala Gly Ser
            180                 185                 190

Lys Gly Glu Ser Gly Asn Lys Gly Glu Pro Gly Ala Val Gly Gln Pro
        195                 200                 205

Gly Pro Pro Gly Pro Ser Gly Glu Glu Gly Lys Arg Gly Ser Thr Gly
    210                 215                 220

Glu Ile Gly Pro Ala Gly Pro Pro Gly Pro Pro Gly Leu Arg Gly Asn
225                 230                 235                 240

Pro Gly Ser Arg Gly Leu Pro Gly Ala Asp Gly Arg Ala Gly Val Met
                245                 250                 255

Gly Pro Ala Gly Ser Arg Gly Ala Thr Gly Pro Ala Gly Val Arg Gly
            260                 265                 270

Pro Asn Gly Asp Ser Gly Arg Pro Gly Glu Pro Gly Leu Met Gly Pro
        275                 280                 285

Arg Gly Phe Pro Gly Ser Pro Gly Asn Ile Gly Pro Ala Gly Lys Glu
    290                 295                 300

Gly Pro Val Gly Leu Pro Gly Ile Asp Gly Arg Pro Gly Pro Ile Gly
305                 310                 315                 320

Pro Ala Gly Ala Arg Gly Glu Pro Gly Asn Ile Gly Phe Pro Gly Pro
                325                 330                 335

Lys Gly Pro Ser Gly Asp Pro Gly Lys Ala Gly Glu Lys Gly His Ala
            340                 345                 350
```

-continued

Gly Leu Ala Gly Ala Arg Gly Ala Pro Gly Pro Asp Gly Asn Asn Gly
            355                 360                 365

Ala Gln Gly Pro Pro Gly Leu Gln Gly Val Gln Gly Gly Lys Gly Glu
    370                 375                 380

Gln Gly Pro Ala Gly Pro Gly Phe Gln Gly Leu Pro Gly Pro Ala
385                 390                 395                 400

Gly Thr Ala Gly Glu Ala Gly Lys Pro Gly Glu Arg Gly Ile Pro Gly
                405                 410                 415

Glu Phe Gly Leu Pro Gly Pro Ala Gly Ala Arg Gly Glu Arg Gly Pro
            420                 425                 430

Pro Gly Glu Ser Gly Ala Ala Gly Pro Thr Gly Pro Ile Gly Ser Arg
        435                 440                 445

Gly Pro Ser Gly Pro Pro Gly Pro Asp Gly Asn Lys Gly Glu Pro Gly
    450                 455                 460

Val Val Gly Ala Pro Gly Thr Ala Gly Pro Ser Gly Pro Ser Gly Leu
465                 470                 475                 480

Pro Gly Glu Arg Gly Ala Ala Gly Ile Pro Gly Gly Lys Gly Glu Lys
            485                 490                 495

Gly Glu Thr Gly Leu Arg Gly Asp Ile Gly Ser Pro Gly Arg Asp Gly
        500                 505                 510

Ala Arg Gly Ala Pro Gly Ala Ile Gly Ala Pro Gly Pro Ala Gly Ala
    515                 520                 525

Asn Gly Asp Arg Gly Glu Ala Gly Pro Ala Gly Pro Ala Gly Pro Ala
    530                 535                 540

Gly Pro Arg Gly Ser Pro Gly Glu Arg Gly Glu Val Gly Pro Ala Gly
545                 550                 555                 560

Pro Asn Gly Phe Ala Gly Pro Ala Gly Ala Ala Gly Gln Pro Gly Ala
                565                 570                 575

Lys Gly Glu Arg Gly Thr Lys Gly Pro Lys Gly Glu Asn Gly Pro Val
            580                 585                 590

Gly Pro Thr Gly Pro Val Gly Ala Ala Gly Pro Ser Gly Pro Asn Gly
        595                 600                 605

Pro Pro Gly Pro Ala Gly Ser Arg Gly Asp Gly Gly Pro Pro Gly Ala
    610                 615                 620

Thr Gly Phe Pro Gly Ala Ala Gly Arg Thr Gly Pro Pro Gly Pro Ser
625                 630                 635                 640

Gly Ile Ser Gly Pro Pro Gly Pro Pro Gly Pro Ala Gly Lys Glu Gly
                645                 650                 655

Leu Arg Gly Pro Arg Gly Asp Gln Gly Pro Val Gly Arg Ser Gly Glu
            660                 665                 670

Thr Gly Ala Ser Gly Pro Pro Gly Phe Val Gly Glu Lys Gly Pro Ser
        675                 680                 685

Gly Glu Pro Gly Thr Ala Gly Pro Pro Gly Thr Pro Gly Pro Gln Gly
    690                 695                 700

Leu Leu Gly Ala Pro Gly Phe Leu Gly Leu Pro Gly Ser Arg Gly Glu
705                 710                 715                 720

Arg Gly Leu Pro Gly Val Ala Gly Ser Val Gly Glu Pro Gly Pro Leu
                725                 730                 735

Gly Ile Ala Gly Pro Pro Gly Ala Arg Gly Pro Pro Gly Asn Val Gly
            740                 745                 750

Asn Pro Gly Val Asn Gly Ala Pro Gly Glu Ala Gly Arg Asp Gly Asn
        755                 760                 765

Pro Gly Asn Asp Gly Pro Pro Gly Arg Asp Gly Gln Pro Gly His Lys

-continued

```
              770                 775                 780
Gly Glu Arg Gly Tyr Pro Gly Asn Ala Gly Pro Val Gly Ala Ala Gly
785                 790                 795                 800

Ala Pro Gly Pro Gln Gly Pro Val Gly Pro Val Gly Lys His Gly Asn
                805                 810                 815

Arg Gly Glu Pro Gly Pro Ala Gly Ala Val Gly Pro Ala Gly Ala Val
                820                 825                 830

Gly Pro Arg Gly Pro Ser Gly Pro Gln Gly Ile Arg Gly Asp Lys Gly
                835                 840                 845

Glu Pro Gly Asp Lys Gly Pro Arg Gly Leu Pro Gly Leu Lys Gly His
                850                 855                 860

Asn Gly Leu Gln Gly Leu Pro Gly Leu Ala Gly His His Gly Asp Gln
865                 870                 875                 880

Gly Ala Pro Gly Ala Val Gly Pro Ala Gly Pro Arg Gly Pro Ala Gly
                885                 890                 895

Pro Ser Gly Pro Ala Gly Lys Asp Gly Arg Ile Gly Gln Pro Gly Ala
                900                 905                 910

Val Gly Pro Ala Gly Ile Arg Gly Ser Gln Gly Ser Gln Gly Pro Ala
                915                 920                 925

Gly Pro Pro Gly Pro Pro Gly Pro Pro Gly Pro Pro Gly Pro Ser Gly
                930                 935                 940

Gly Gly Tyr Glu Phe Gly Phe Asp Gly Asp Phe Tyr Arg Ala Asp Gln
945                 950                 955                 960

Pro Arg Ser Pro Thr Ser Leu Arg Pro Lys
                965                 970
```

METHOD FOR PREPARING A THREE-DIMENSIONALLY CULTURED SKIN COMPRISING DERMIS AND EPIDERMIS, AND THE CULTURED SKIN MADE THEREFROM

CROSS-REFERENCE TO RELATED APPLICATIONS

This application is the National Stage of International Application No. PCT/KR2015/007118, filed on Jul. 9, 2015 claiming the priority of KR 10-2014-0086148, filed on Jul. 9, 2014, the content of each of which is incorporated by reference herein.

TECHNICAL FIELD OF THE INVENTION

The present invention relates to a method for preparing a three-dimensionally cultured skin model comprising dermis and epidermis and includes a step of preparing the dermis with murine fibroblasts and either native collagen alone or a combination of native collagen and atelocollagen, and a step of forming the epidermis using keratinocytes. The present invention also relates to a three-dimensionally cultured skin model composed of dermis, which is prepared using a composition containing murine fibroblasts and either native collagen alone or a combination of native collagen and atelocollagen, and epidermis, which is formed from keratinocytes.

BACKGROUND OF THE INVENTION

The human skin is the largest organ that covers the entire surface of the body. The skin has various functions including temperature control, protection from external environments, etc., and has a surface area of about 1.2 $m^2$ to about 2.3 $m^2$ in adults. The skin is composed of epidermis and dermis. The dermis is composed of collagen and fibroblasts and the epidermis is composed of keratinocytes, melanocytes, etc. Unlike the epidermis, which has a relatively constant thickness, the thickness of the dermis is known to vary greatly depending on the area and is also about 3 times thicker than the epidermis. The epidermis is stratified into sublayers of basement membrane, stratum spinosum, stratum granulosum, and stratum corneum, and many layers of final-differentiated dead cells are amassed on the skin surface to serve a protective function. The basement membrane is in the form of a thin membrane, in which laminin and several extracellular substrates are deposited on a type 4 collagen lattice, and the cells of the stratum basale are attached thereto. Skin damage accompanies decomposition of the basement membrane and allows the cells in the stratum basale to be in contact with type 1 collagen, during which the epidermal cells migrate to the sides, thereby inducing re-epithelialization.

The dermis has many fibroblasts and is composed of papillary dermis (in which microvessels are distributed) and reticular dermis (in which many thick collagen fibers are present). Hair follicles and various auxiliary organs of the skin are located deep in the skin. Accordingly, in a case when the epidermis is lost due to a partial thickness wound, the epidermal cells will grow out of the hair follicles and induce re-epithelialization.

Meanwhile, there have been attempts to constitute artificial skin tissue. Artificial skin can generally be used for replacing damaged skin which has lost its ability to regenerate by self-cells, skin ulcers, or toxicity and efficacy experiments of pharmaceutical drugs or cosmetics, etc. Artificial skin is very important for the development of a skin substitute to replace damaged human skin or a pharmaceutical drug for the treatment thereof, or as an experimental material for toxicity and efficacy tests of a medical device designed to contact with skin, daily essentials, cosmetics, etc.

Accordingly, for such utilization, there is a need for the development of artificial skin having a structure mimicking a natural skin layer. In Europe, the sales of cosmetics manufactured through animal experiments have been completely prohibited since 2013, and thus leading global cosmetics companies are making a heavy investment on the development of artificial skin. For example, Episkin®, self-developed by L'Oreal France, has passed the European Standard for artificial skin, being acknowledged as an artificial skin to completely replace animal experiments, and EpiDerm®, developed by MatTek Corporation in the USA, has acquired only a provisional approval because it shows excessive reaction to human skin. Examples of the representative methods for preparing artificially cultured skin models developed so far may include: a method for preparing reconstructed epidermis on de-epidermized dermis (RE-DED), in which human keratinocytes are cultured three-dimensionally on the dermis where the epidermis is removed; and a method of living skin equivalent (LSE), in which human keratinocytes are cultured on a collagen substrate containing fibroblasts.

However, the three-dimensionally cultured skins developed so far have disadvantages in that a basement membrane is not fully formed between the dermis prepared with collagen and the epidermis and that dermal contraction takes place during the culture process. Therefore, there is still a need for a technology for preparing a three-dimensionally cultured skin that can more closely mimic human skin.

SUMMARY OF THE INVENTION

Under the circumstances, the present inventors have made efforts to develop a three-dimensionally cultured skin similar to the human skin layers that can be used for toxicity and efficacy tests of pharmaceutical drugs or cosmetics. As a result, they have discovered that dermal contraction can be overcome by using murine 3T3 cells and a mixture of atelocollagen and native collagen, thereby preparing a three-dimensionally cultured skin model that can replace experimental animals, and thereby completing the present invention.

An object of the present invention is to provide a method for preparing a three-dimensionally cultured skin model composed of dermis and epidermis, including: inoculating a composition, which contains murine fibroblasts; and either native collagen or a combination of native collagen and atelocollagen, into a culture dish and solidifying the same to prepare the dermis; inoculating keratinocytes into the upper layer of the dermis prepared in the above step and culturing until a cell sheet is formed thereon; and exposing the cell sheet formed in the above step in the air to form the epidermis.

Another object of the present invention is to provide a three-dimensionally cultured skin model comprising: the dermis prepared by using a composition, which includes murine fibroblasts, and native collagen or a combination of native collagen and atelocollagen; and the epidermis formed by keratinocytes.

The three-dimensionally cultured skin model of the present invention can be widely used in toxicity and efficacy tests of medicines or cosmetics, and in the field of alternative tests for animal experiments, because the three-dimensionally cultured skin model exhibits excellent formation and differentiation of dermis and epidermis by using murine 3T3 cells for preparing the skin model and a mixture of atelocollagen and native collagen, and also has a structure similar to the human skin layers by inhibiting contraction and degradation of collagen in the dermis.

In the present invention, confluency refers to a state in which the culture surface is entirely covered with cells.

Figure 4:
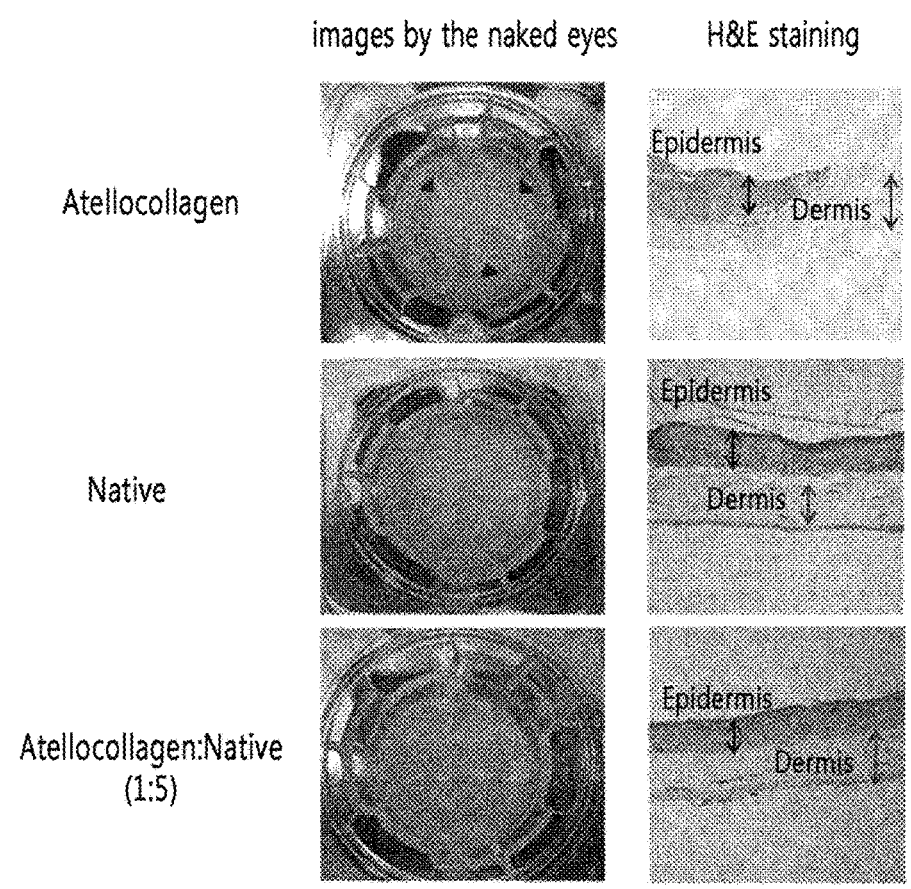

FIG. 4 shows images confirming the structures of three-dimensionally cultured skin models in Experimental Group 1 (in which the dermis was prepared by using atelocollagen only), Experimental Group 2 (in which the dermis was prepared by using native collagen only), and Experimental Group 3 (in which the dermis was prepared by mixing atelocollagen with native collagen at a 1:5 ratio), by H & E staining. The contraction of collagen is indicated by '▶'.

Figure 5:
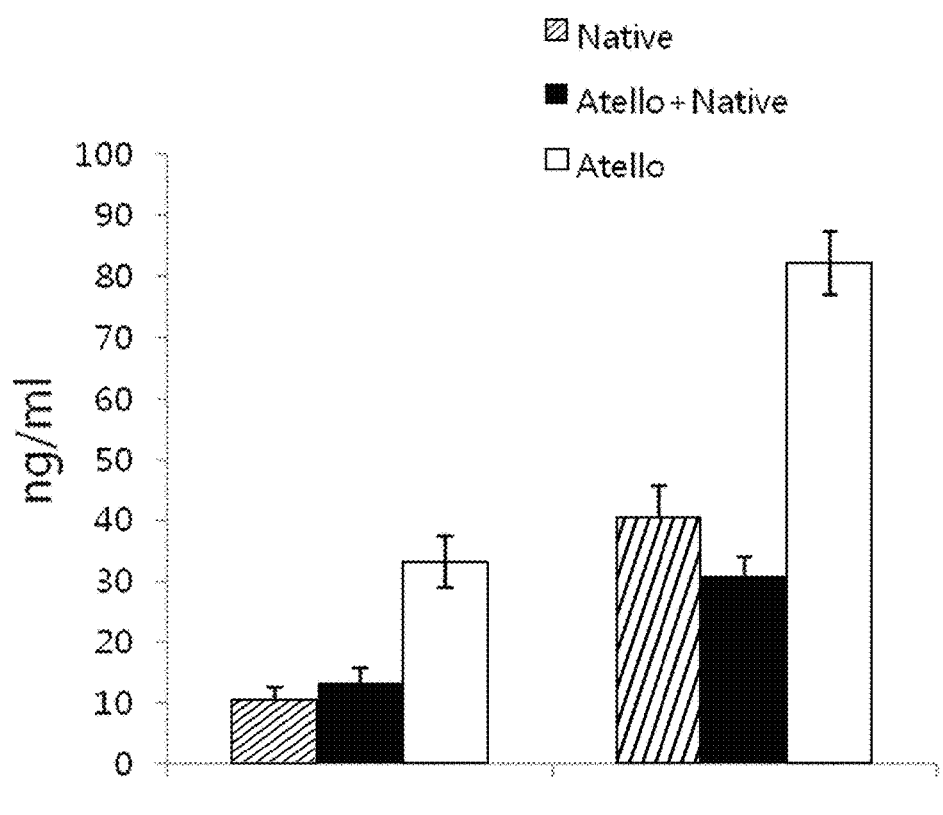

FIG. 5 shows graphs confirming the expression of MMP-2 and MMP-9 in the culture medium, where each of the three-dimensionally cultured skin of Experimental Group 1 (in which the dermis was prepared by using atelocollagen only), Experimental Group 2 (in which the dermis was prepared by using native collagen only), and Experimental Group 3 (in which the dermis was prepared by mixing atelocollagen with native collagen at a 1:5 ratio) were cultured.

Figure 6:
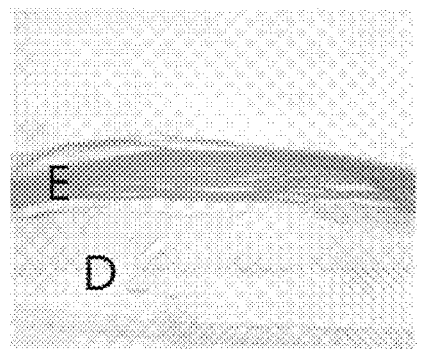
Figure 6:
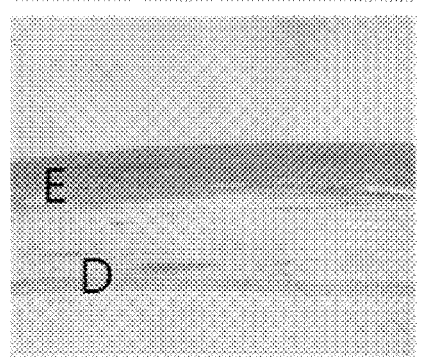
Figure 6:
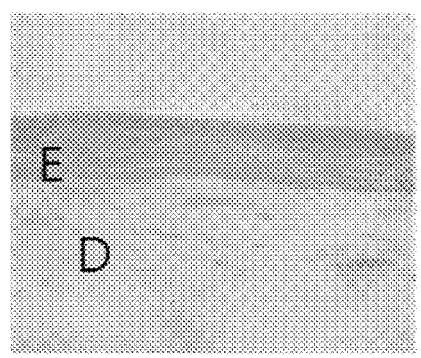

FIG. 6 shows H & E stained images confirming the structures of three-dimensionally cultured skin models in which the dermis was prepared by mixing atelocollagen with native collagen at a ratio of 1:1, 1:5, or 1:10.

Figure 7:
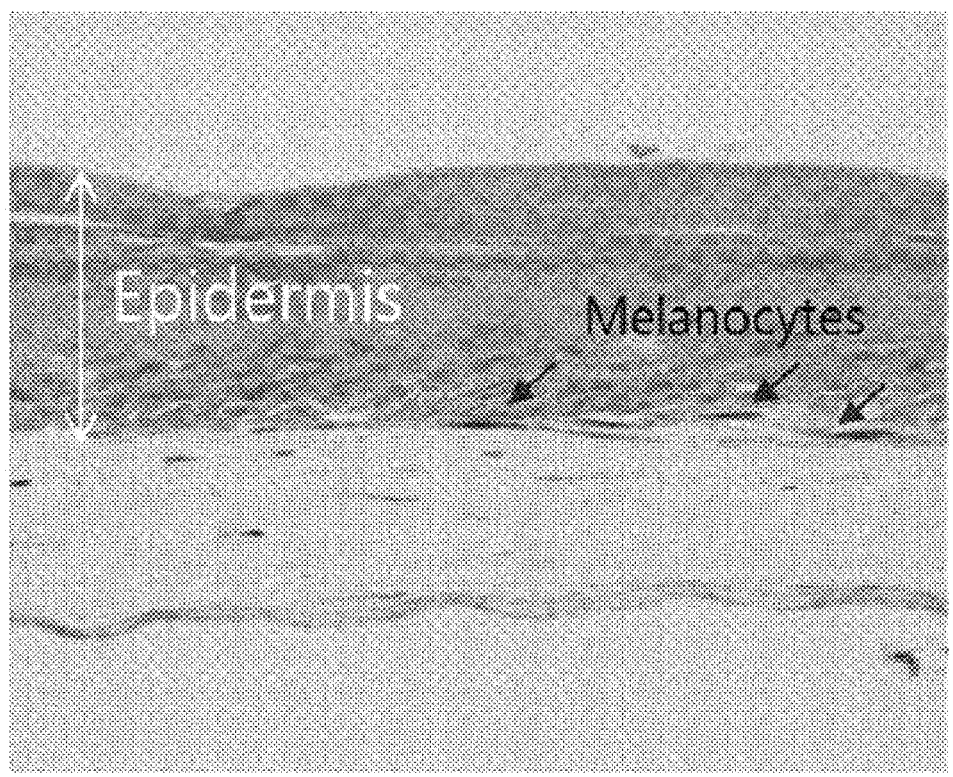

FIG. 7 shows an H & E stained image confirming the structure of a three-dimensionally cultured skin model in which melanocytes were added when the epidermis was prepared.

Figure 8:
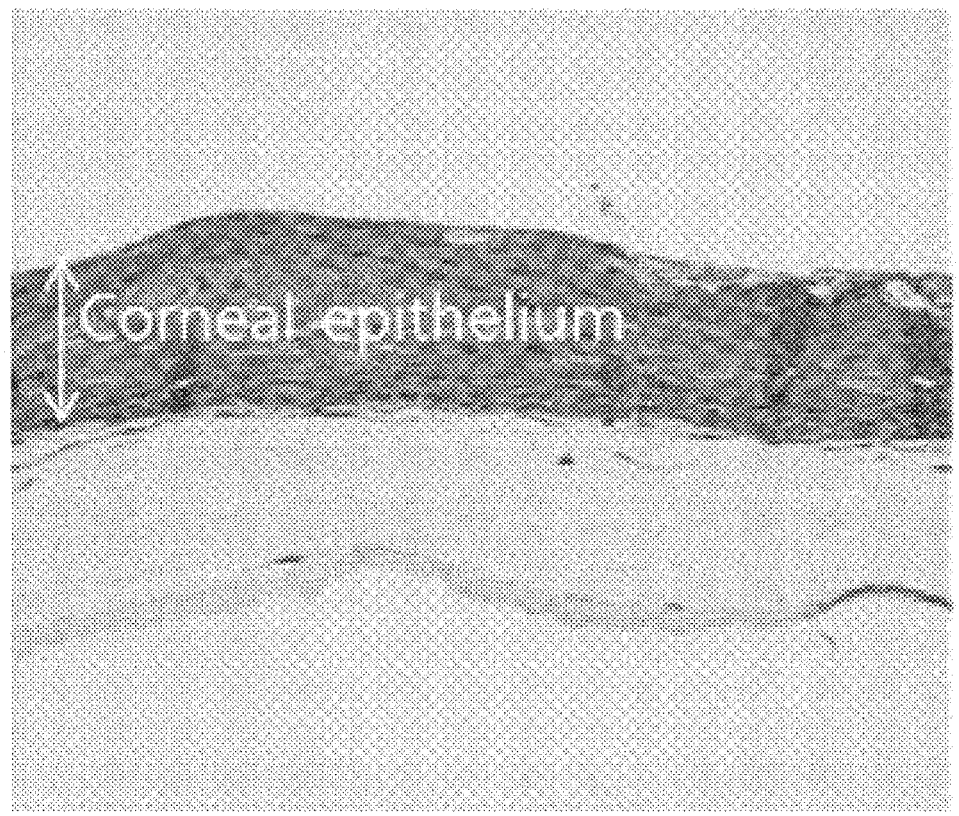

FIG. 8 shows an H & E stained image confirming the structure of a three-dimensionally cultured skin model in which the epidermis was prepared by corneal epithelial cells (also known as keratinocytes from cornea).

Figure 9:
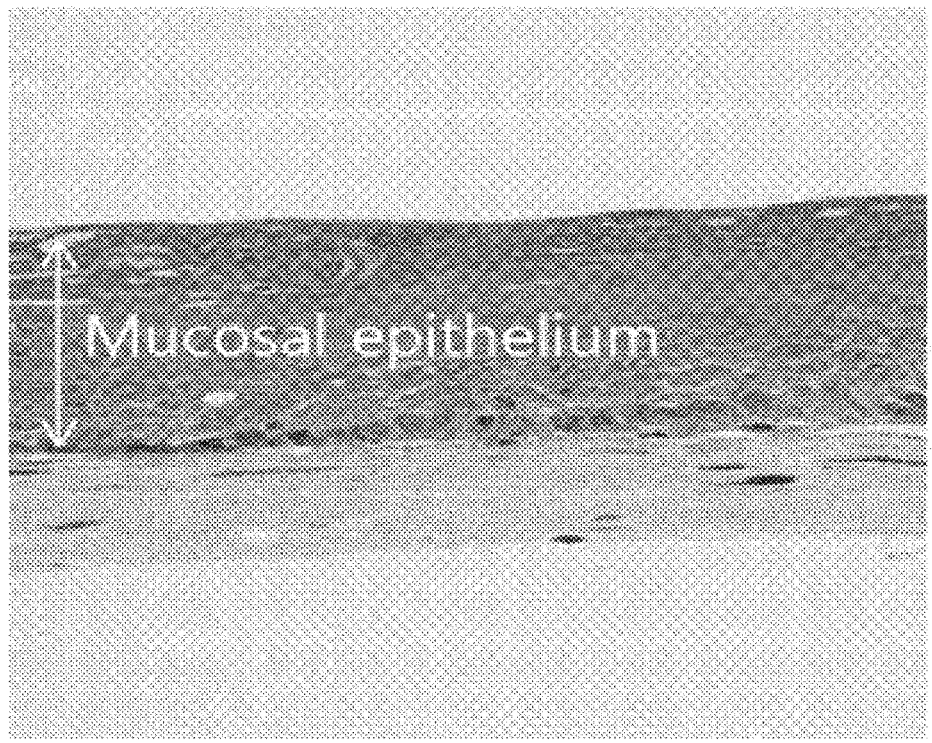

FIG. 9 shows an H & E stained image confirming the structure of a three-dimensionally cultured skin model in which the epidermis was prepared by oral mucosal keratinocytes.

DETAILED DESCRIPTION OF THE INVENTION

To achieve the above objects, in an aspect, the present invention provides a method for preparing a three-dimensionally cultured skin model comprised of dermis and epidermis, including: preparing the dermis by using a composition containing native collagen or a combination of native collagen and atelocollagen; and preparing the epidermis by using keratinocytes.

Specifically, the present invention provides a method for preparing a three-dimensionally cultured skin model consisting of dermis and epidermis, including: (a) inoculating a composition, which contains murine fibroblasts; and native collagen or a combination of native collagen and atelocollagen, into a culture dish and solidifying the same to prepare the dermis; (b) inoculating keratinocytes on the dermis prepared in the above step and culturing until confluent; and (c) raising it to the air/liquid interface to form the upper layers of epidermis.

The present invention is characterized in that, in the process of preparing a three-dimensionally cultured skin model consisting of dermis and epidermis, the dermis was prepared by using a composition containing murine fibroblasts, and either native collagen only or a combination of native collagen and atelocollagen, and as a result, the formation and differentiation of the epidermis were optimized and the dermal contraction was inhibited, thereby resulting in a three-dimensionally cultured skin having a similar structure to the human skin.

As used herein, the term "fibroblast" refers to a cell which makes up an important component of fibrous connective tissue, and in particular, refers to a major cell constituting the dermis with respect to the skin associated with the present invention. In the present invention, the fibroblast may be derived from humans, mice, rats, etc., but the origin is not limited thereto. For the purpose of the present invention, in the process of preparing a three-dimensionally cultured skin model, the fibroblasts to be used for preparing the dermis may be, in particular, murine fibroblasts, e.g., 3T3-J2, NIH3T3, 3T6, 3T12, 3T12A, or 6T6 cell lines, or representatively, 3T3-J2, which is a murine fibroblast cell line. Additionally, the fibroblasts of the present invention may be those derived from normal tissue or from lesions such as chemical and flame burns, wounds, scars, ulcers, etc., but is not limited thereto.

As used herein, the term "keratinocyte" refers to a cell which expresses cytokeratin. Keratinocytes constitute the majority of the cells in the epidermis or epithelium. In the present invention, keratinocytes may be derived from humans, mice, rats, etc., but are not limited thereto. For the purpose of the present invention, in the process of preparing a three-dimensionally cultured skin model, keratinocytes to be used for preparing the epidermis may be, in particular, human keratinocytes, and in particular, may be keratinocytes derived from normal tissue or keratinocytes derived from lesions such as chemical and flame burns, wounds, scars, ulcers, etc., but are not limited thereto.

Figure 1:
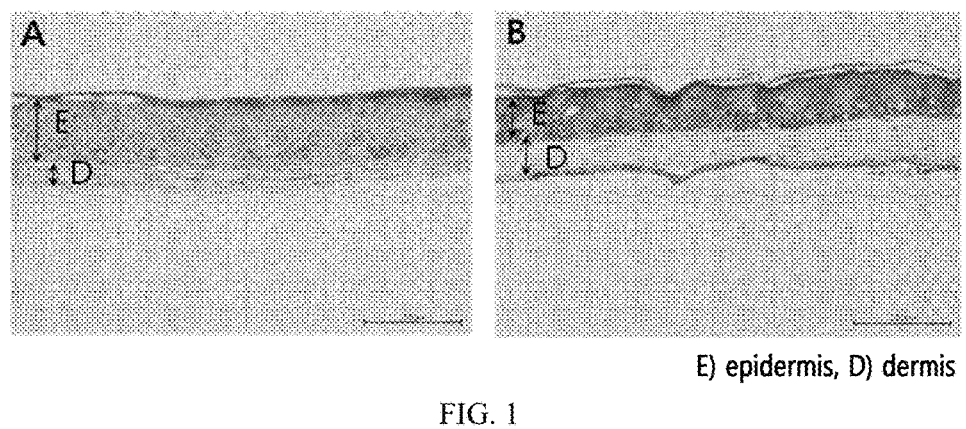
FIG. 1 shows images of the structures of three-dimensionally cultured skin models, in which the dermis was respectively prepared by using human fibroblasts (A) or murine fibroblast 3T3 cells (B), confirmed by Hematoxylin & Eosin (H & E) staining.

In a specific embodiment of the present invention, the dermis of a three-dimensionally cultured skin model was prepared using murine fibroblasts (representatively by using the 3T3-J2 cell line) or human fibroblasts (Example 2-1). It was confirmed that the dermis prepared using murine fibroblasts was consistently about twice as thick as that prepared using human fibroblasts. On the other hand, when the dermis is prepared using human fibroblasts, the collagen in the resulting dermis is rapidly degraded, thus making the dermis thinner than that prepared using murine fibroblasts. When prepared on the dermis containing murine fibroblasts, the basal layer was clearly identified in the epidermis comprising all of the epidermal layers (FIG. 1).

Figure 2:
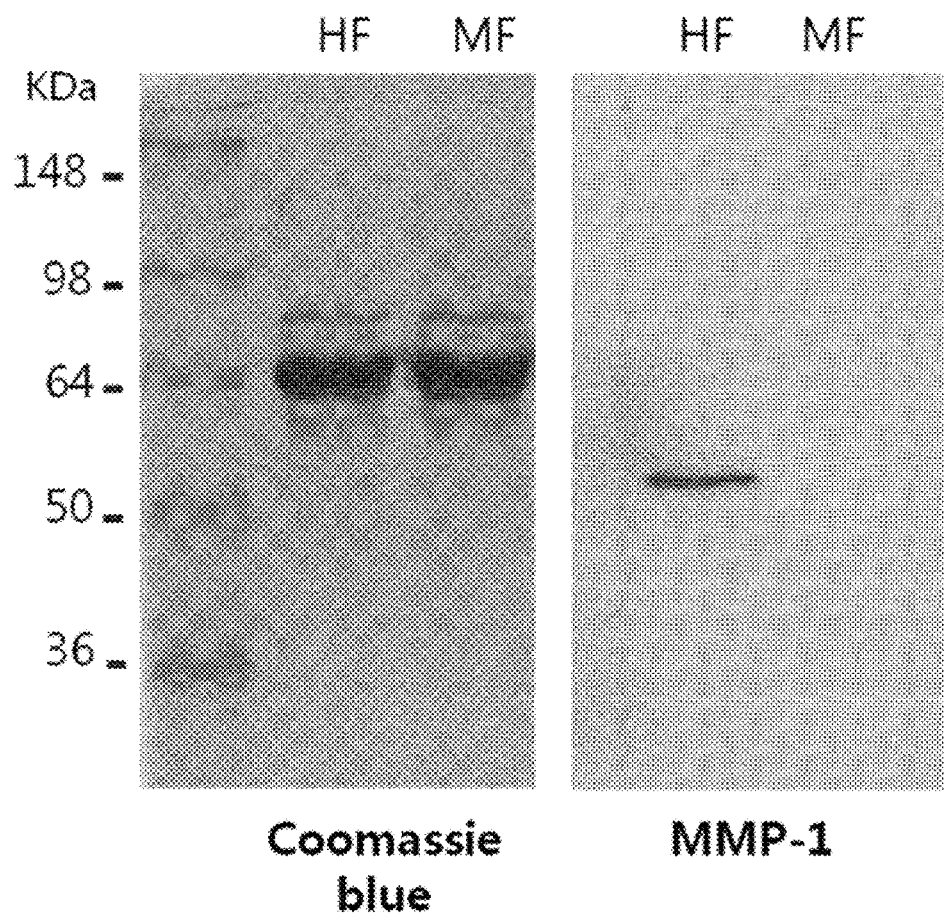
FIG. 2 shows images confirming the expression matrix metalloproteinase-1 (MMP-1) in three-dimensionally cultured skin models, in which the dermis was prepared by using either human fibroblasts (HF) or murine fibroblast 3T3 cells (MF).
Figure 3:
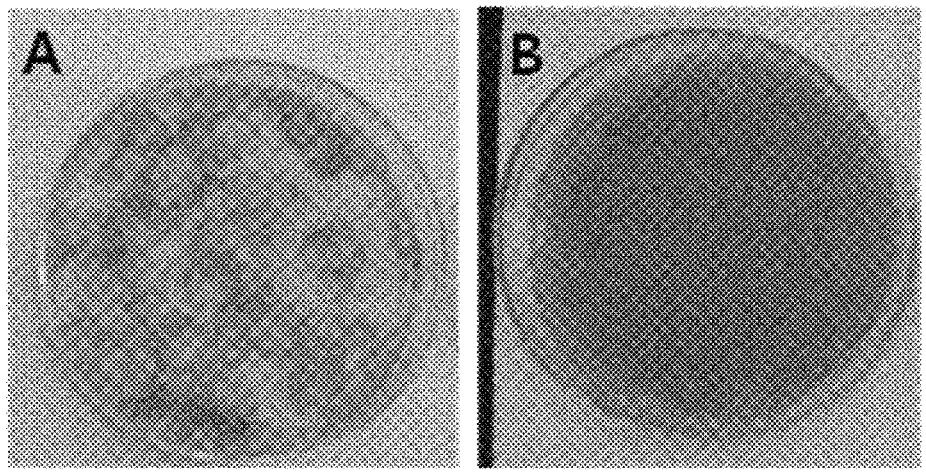
FIG. 3 shows images confirming the sheet-forming ability (the rate to reach confluency) of keratinocytes in three-dimensionally cultured skin models, in which the dermis was prepared by using either human fibroblasts (HF) or murine fibroblast 3T3 cells (MF).

Additionally, in a specific embodiment of the present invention, the expression of MMP-1 (54 kDa) was observed only when human fibroblasts were used while the expression of MMP-1 (54 kDa) was not observed when murine fibroblasts were used (FIG. 2). Furthermore, when the dermis was prepared using murine fibroblasts, sheet-forming ability was higher than that with human fibroblasts (FIG. 3).

In a specific embodiment of the present invention, it was confirmed that the formation of dermis using murine fibroblasts, compared to the formation of dermis using human fibroblasts, exhibited i) a more stable dermal structure, ii) a consistently thicker collagen layer, and iii) more rapid formation of cell sheets. The results indicate that when the dermis is prepared using murine fibroblasts, not only is the resulting dermis more morphologically similar to human skin, but also the time required for the preparation of a three-dimensionally cultured skin model is reduced.

In connection with the present invention, in particular, the three-dimensionally cultured skin model for use in the toxicity and efficacy experiments of pharmaceutical drugs and cosmetics is frequently required to be produced on a large scale. Therefore, the effects of decreasing the required number of keratinocytes or reducing the preparation time for a three-dimensionally cultured skin model appear to be very meaningful. Additionally, the three-dimensionally cultured skin model prepared in the present invention can be used not only for the toxicity and efficacy tests but also as pharmaceutical drugs for skin grafting and wound treatment.

The method for preparing a three-dimensionally cultured skin model of the present invention may be a method in which dermis is formed by using the murine fibroblasts of the present invention to exhibit at least one of the following characteristics compared to when human fibroblasts are used:
 i) increase in stability of dermal structure;
 ii) increase in epidermal differentiation;
 iii) inhibition of dermal contraction;
 iv) inhibition of collagen degradation;
 v) decrease in the level of MMP expression; and
 vi) increase in sheet-forming ability.

As used herein, the term "collagen" refers to a scleroprotein present in both plants and animals, and in particular, it is mainly present in animal bones and skin, also distributed in cartilages, organs, membranes, hairs, etc., and is also called a collagenous material. Collagen is a protein consisting of a triple helix which has non-helical telopeptides at both ends. In the present invention, collagen may be derived from humans, cows, pigs, mice, rats, etc., but is not limited thereto. In the present invention, collagen may be native collagen, bioengineering mutation, or collagen modified by bioengineering and chemical methods, but the collagen is not limited to the origin and presence of the modification described above.

As used herein, the term "atelocollagen" refers to collagen in which telopeptides, a major cause of inducing immune responses, are removed. Atelocollagen may be produced by treating collagen, which is extracted from colloids in cows or pigs, with an enzyme capable of removing telopeptides or by using a recombinant technology. Atelocollagen is a type of collagen with reduced immunogenicity. Atelocollagen has no antigenicity, good biocompatibility, and can be metabolized and absorbed within a short period of time. Accordingly, atelocollagen is known as a biomaterial and is widely used in applied fields such as artificial skin, artificial blood vessels, carriers in tissue culture, and cosmetics.

For the purpose of the present invention, the collagen contained in the dermis of a three-dimensionally cultured skin model of the present invention may be native collagen or a combination of native collagen and atelocollagen. The native collagen may be one which includes alpha-1 chain consisting of the amino acid sequence of SEQ ID NO: 1 and alpha-2 chain consisting of the amino acid sequence of SEQ ID NO: 2. The atelocollagen may be one which includes alpha-1 chain consisting of the amino acid sequence of SEQ ID NO: 3 and alpha-2 chain consisting of the amino acid sequence of SEQ ID NO: 4. Additionally, in the present invention, the combination ratio between atelocollagen and native collagen may be in a range of 1:0.1 to 1:20, and preferably 1:0.5 to 1:15.

According to a specific embodiment of the present invention, the dermis of a three-dimensionally cultured skin model was prepared using atelocollagen alone, native collagen alone, and a combination of atelocollagen and native collagen (Example 3-1). Specifically, Experimental Group 1 (in which the dermis was prepared by using atelocollagen only), Experimental Group 2 (in which the dermis was prepared by using native collagen only), and Experimental Group 3 (in which the dermis was prepared by mixing atelocollagen with native collagen at a 1:5 ratio) were prepared. As a result, it was confirmed that the existing problems of collagen contraction due to the use of atelocollagen alone, and the epidermis formation and decrease of differentiation could be overcome by adding native collagen (atelocollagen:native collagen=1:5) (FIG. 4). Additionally, Experimental Group 1 (atelocollagen only) showed significantly higher expression levels of MMP-2 and MMP-9, which are at least 2-fold higher compared to those of Experimental Groups 2 and 3, whereas Experimental Group 3 (in which the dermis was prepared by mixing atelocollagen with native collagen) showed low expression levels of MMP-2 and MMP-9, which were similar to those of a case where only native collagen was used (FIG. 5).

Additionally, according to a specific embodiment of the present invention, when the three-dimensionally cultured skin model was prepared by varying the mixing ratio between atelocollagen and native collagen, it was confirmed that artificial skin tissue was stably prepared until the mixing ratio was within the range of 1:1 to 1:10 (FIG. 6).

The method for preparing a three-dimensionally cultured skin model of the present invention may be a method in which dermis is formed by native collagen or a combination of native collagen and atelocollagen to exhibit at least one of the following characteristics compared to when atelocollagen is used alone:
 i) inhibition of dermal contraction;
 ii) increase in epidermal differentiation;
 iii) decrease in the level of MMP expression; and
 iv) inhibition of collagen degradation.

As used herein, the term "a three-dimensionally cultured skin model" refers to a skin model prepared by an artificial culture process to mimic the morphology and the physiology of human skin. The origin of the cells constituting the model is not limited. For the purpose of the present invention, the three-dimensionally cultured skin model is not limited as long as the model includes the dermis consisting of collagen and fibroblasts and the epidermis consisting of keratinocytes.

In the method for preparing a three-dimensionally cultured skin model of the present invention, the composition containing murine fibroblasts and native collagen or a combination of native collagen and atelocollagen in step a) may include $1\times10^4$ to $1\times10^7$ murine fibroblasts per $cm^2$, and in particular, $1\times10^5$ to $1\times10^6$ fibroblasts. Additionally, in step a) above, the composition may further contain at least one cell selected from the group consisting of human fibroblasts, dermal papilla cells, endothelial cells, adipocytes, and mesenchymal stem cells.

In a specific embodiment of the present invention, in the step for preparing the dermis according to the preparation method of a three-dimensionally cultured skin model, the composition containing murine fibroblasts; native collagen; or a combination of native collagen and atelocollagen was prepared by containing the murine fibroblasts in an amount of $0.5 \times 10^5$ fibroblasts per $cm^2$.

Additionally, step a) of the preparation method of a three-dimensionally cultured skin model may be performed for 1 hour to 48 hours. In a specific embodiment of the present invention, the step of inoculating the composition containing murine fibroblasts and collagen corresponding to step a) above into a 6-well plate and solidifying the same was performed overnight (for about 12 hours).

In the method for preparing a three-dimensionally cultured skin model of the present invention, $1 \times 10^4$ to $1 \times 10^7$ keratinocytes per $cm^2$ of the dermis prepared in step a) may be inoculated in step b). In a specific embodiment of the present invention, in the step of inoculating keratinocytes on the dermis and culturing them until a cell sheet is formed thereon, which corresponds to step b) above, about $2.5 \times 10^5$ keratinocytes were inoculated per well (4.7 $cm^2$) of a 6-well plate.

Additionally, in step b) above, the keratinocytes may be derived from the skin, mucosa, cornea, or hair follicles, but are not limited thereto. At least one cell selected from the group consisting of melanocytes, Merkel cells, and Langerhans cells may be inoculated, and not only normal cells but cells derived from a disease may be used for a three-dimensionally cultured skin model with respect to diseases.

In a specific embodiment of the present invention, it was confirmed that, in step c) preparing epidermis, as a result of preparing the three-dimensionally cultured skin model of the present invention, in a case where corneal epithelial cells or oral mucosal keratinocytes were inoculated and melanocytes were inoculated simultaneously along with keratinocytes, a stable three-dimensionally cultured skin model was prepared (FIGS. 7 to 9).

Additionally, step b) above may be performed for about 2 days to about 7 days, but is not particularly limited thereto because it may vary depending on the keratinocytes for inoculation, the area of dermis, etc.

In the present invention, the period for forming the corresponding cell sheet may be shortened by using the dermis containing murine fibroblasts, native collagen, or a combination of native collagen and atelocollagen. In a specific embodiment of the present invention, it was confirmed that the sheet-forming ability was excellent when murine fibroblasts were used compared to when human fibroblasts were used (FIG. 3). Since when the epidermis is prepared using human fibroblasts, the time-point for sheet-forming or air-lifting may be delayed or require a higher amount of keratinocytes for the initial inoculation, and thus the result confirmed the excellence of using murine fibroblasts of the present invention.

In the method for preparing a three-dimensionally cultured skin model of the present invention, step c) above may be performed for 7 days to 21 days. In a specific embodiment of the present invention, the step of inducing epidermal differentiation by raising it to the air/liquid interface, which corresponds to step c) above, was performed for about 12 days (Example 2-2).

The methods for isolating and culturing cells of the present invention are not particularly limited but any conventional method known may be used. For example, in the step of culturing keratinocytes, the conditions for the cultivation are not particularly limited but any conventional conditions for in-vivo cells and any medium and culture temperature suitable for in-vivo culture may be used without limitation.

In another aspect, the present invention provides a three-dimensionally cultured skin model comprising: the dermis prepared by using a composition, which contains murine fibroblasts; and native collagen or a combination of native collagen and atelocollagen; and the epidermis formed by keratinocytes.

In the present invention, fibroblasts, collagen, the three-dimensionally cultured skin model, etc. are the same as explained above.

The three-dimensionally cultured skin model according to the present invention may be effectively used in performing physiological, molecular biological, and biochemical studies associated with the skins of animals including humans. Additionally, the three-dimensionally cultured skin model may be used for the efficacy and toxicity tests of materials which are expected to be conventionally in contact with skins. The materials expected to be conventionally in contact with skins encompass all the materials such as pharmaceutical drugs (especially, drugs for external use), cosmetics, fibers, detergents, etc., and representatively include those which are used for the efficacy and toxicity tests of pharmaceutical drugs or cosmetics. Additionally, the three-dimensionally cultured skin model according to the present invention may be used as a disease model for damaged tissue due to chemicals, burns, wounds, scars, ulcers, etc., as well as for the efficacy and toxicity tests in normal skin conditions. Additionally, the three-dimensionally cultured skin model prepared according to the present invention may be used as a substitute for experimental animals. Additionally, the three-dimensionally cultured skin model prepared according to the present invention may be used as pharmaceutical drugs for grafting and wound treatment instead of for simple experiments.

The three-dimensionally cultured skin model according to the present invention has a constitution close to the human skin layer and thus it may be used as an alternative of a skin model to meet the global demand for the substitute of experimental animals.

Hereinafter, the present invention will be described in more detail with reference to the following Examples. However, these Examples are for illustrative purposes only, and the invention is not intended to be limited by these Examples.

Example 1. Materials Used for the Preparation of a Three-Dimensionally Cultured Skin Model Comprising Dermis and Epidermis In the present invention, experiments were performed for the preparation of a three-dimensionally cultured skin model comprising dermis and epidermis and possessing characteristics that are closest to the human skin. The materials used for the preparation of a basic three-dimensionally cultured skin model are as follows.

Experimental Materials
Murine fibroblasts (3T3 cell line) or Human fibroblasts
Human Keratinocytes
Collagen (atelocollagen and/or native collagen)
Transwell insert (6 well)

Maintenance tray
DMEM/F12 medium containing 10% FBS
Epidermal Growth Factor (EGF)

A three-dimensionally cultured skin model comprising dermis and epidermis was prepared using the above materials.

Example 2. Preparation of a Three-Dimensionally Cultured Skin Model Comprising Dermis and Epidermis 2-1. Preparation of Dermis (Collagen Dermis)

Murine fibroblast 3T3 cells or human fibroblasts were mixed with a 2.0 mg/mL collagen solution and 10× reconstruction buffer (0.2 M sodium bicarbonate, 0.2 M HEPES, 0.05 N NaOH) to prepare a cell mixture solution to a concentration of $1 \times 10^5$ cells/mL. The cell mixture solution was added into a 6-well transwell insert in an amount of 2 mL per well. The mixture solution was solidified in an incubator (37° C., 10% $CO_2$) overnight (1 hour to 24 hours).

2-2. Preparation of Epidermis (Epidermis Setting)

Keratinocytes were inoculated in a concentration of $2.5 \times 10^5$ cells on the dermis prepared in Example 2-1. The keratinocytes were cultured in an incubator (37° C., 10% $CO_2$) for about 5 days to 6 days until the keratinocytes formed a sheet while replacing the medium with a fresh medium containing 10 ng/mL EGF at 2-day intervals. Upon formation of a sheet of keratinocytes on the dermis, the resultant was transferred into a 6-well type maintenance tray for air-lifting. Then, the tray was filled with the EGF-containing medium, and the thus-prepared dermis-epidermis was subjected to air-lifting.

Meanwhile, in the preparation of epidermis, the three-dimensionally cultured model of the present invention was prepared by inoculating with corneal epithelial cells or oral mucosal keratinocytes or simultaneously inoculating with both keratinocytes and melanocytes.

Then, the medium was cultured for a total of 14 days while replacing the medium with a fresh medium containing 10 ng/mL EGF at 4-day intervals.

2-3. Histological Analysis (H & E Staining)

The structure of the three-dimensionally cultured skin model prepared in Example 2-2 was examined by Hematoxylin & Eosin (H & E) staining.

H & E staining was performed using an experimental process widely known in the art.

As a result, as can be confirmed in FIG. 1, the dermis prepared by using murine fibroblasts was about two times thicker than that prepared using human fibroblasts, and also the dermis prepared by using murine fibroblasts formed a stable skin model with a uniform tissue thickness. However, when the dermis was prepared using human fibroblasts, the initial collagen thickness was not maintained but degraded, thus resulting in formation of a very thin dermal layer.

On the contrary, it was confirmed that the murine fibroblasts formed epidermis and dermis at a 1:1 thickness ratio and also formed epidermis with a uniform and stable shape. Furthermore, stratum basale, stratum spinosum, stratum granulosum, and stratum corneum should be formed in the epidermis. When the epidermis was prepared on the dermis containing murine fibroblasts, the basal layer was clearly identified in the epidermis composed of all the epidermal layers.

Additionally, as the results of the inoculation with corneal epithelial cells or oral mucosal keratinocytes or simultaneously inoculating with both keratinocytes and melanocytes during the preparation of epidermis, it was confirmed that a stable three-dimensionally skin model could be prepared by including the additionally inoculated cells (FIGS. 7 to 9).

These results confirmed that the dermis prepared by using murine fibroblasts can prepare a more uniform and stable skin model compared to that prepared using human fibroblasts. Accordingly, it was attempted to confirm the cause of the difference in stable dermal thickness.

2-4. MMP-1 Expression

For the analysis of the cause(s) of histological difference confirmed by histological staining in Example 2-3, the expression level of MMP-1, among MMPs which degrade collagen, etc., was measured in medium cultured for 2 days during the preparation of the three-dimensionally cultured skin model using murine or human fibroblasts.

The level of MMP-1 expression was measured by western blotting, which was performed by using a method widely known in the art.

As can be confirmed in FIG. 2, the expression of MMP-1 (54 kDa) was observed only when human fibroblasts were used, whereas the expression of MMP-1 was not observed when murine fibroblasts were used. Accordingly, it can be confirmed that the dermal contraction confirmed in Example 2-3 takes place due to the degradation of collagen by MMP-1.

2-5. Effect on the Formation of Epidermis—Sheet-Forming Abilities

The sheet-forming abilities of keratinocytes, where murine fibroblasts or human fibroblasts were co-cultured, were compared. Specifically, murine fibroblasts or human fibroblasts were inoculated into a cell culture container (size: 58 $cm^2$) and, on top of the fibroblasts, keratinocytes ($1 \times 10^5$ cells) were inoculated. The resultant was stained with rhodamine solution on the 11th day of culture and the presence of cell sheet formation was examined.

As a result, as can be confirmed in FIG. 3, when murine fibroblasts (B) were used, the entire surface of the culture container was stained, thus confirming that a cell sheet was formed on the 11th day from the inoculation, whereas when human fibroblasts (A) were used, it was observed that a complete cell sheet was not formed.

These results confirm that when epidermis is prepared using human fibroblasts, the time-point for air-lifting may be delayed or a higher amount of keratinocytes for initial inoculation may be required, compared to when epidermis is prepared using murine fibroblasts.

2-6. Conclusion

As reviewed above, it was confirmed that the formation of dermis using murine fibroblasts, compared to the formation of dermis using human fibroblasts, exhibited i) a more stable dermal structure ii) a consistently thicker collagen layer, and iii) more rapid formation of cell sheets. The results indicate that when the dermis is prepared using murine fibroblasts, not only does the resulting three-dimensionally cultured skin model have histological morphology similar to that of human skin, but also the time required for the preparation of the model can be reduced.

In the present invention, in particular, the three-dimensionally cultured skin model for use in the toxicity and efficacy experiments of pharmaceutical drugs and cosmetics is frequently required to be produced on a large scale. Therefore, the effects of decreasing the required number of keratinocytes or reducing the preparation time for a three-dimensionally cultured skin model are very meaningful.

Example 3. Optimization of the Preparation of a Three-Dimensionally Cultured Skin Model According to Collagen Types In Example 2, the excellent effects of using murine fibroblasts in preparing the three-dimensionally cultured skin model of the present invention were confirmed. In addition, the present inventors attempted to optimize collagen, another dermis-forming factor, for optimizing the preparation of the three-dimensionally cultured skin model.

3-1. Optimization Using Native Collagen and Atelocollagen

The collagen used includes native collagen and atelocollagen, which has lower immunogenicity compared to that of native collagen. Specifically, dermis was prepared in Experimental Group 1 (in which the dermis was prepared by using atelocollagen only), Experimental Group 2 (in which the dermis was prepared by using native collagen only), and Experimental Group 3 (in which the dermis was prepared by mixing atelocollagen with native collagen at a 1:5 ratio) and compared.

As a result, as can be confirmed in FIG. 4, in Experimental Group 1 (in which the dermis was prepared by using atelocollagen only), the contraction of collagen is indicated by '▶'.

In contrast, dermal contraction was not observed in Experimental Group 3 (in which the dermis was prepared by mixing atelocollagen with native collagen at a 1:5 ratio), and the fully-differentiated epidermis was confirmed.

These results suggest that the use of atelocollagen, which has no immunogenicity, is useful in preparing a three-dimensionally cultured skin model; however, significant problems of serious dermal contraction and subsequent formation of epidermis and decrease of differentiation can be overcome by adding native collagen (atelocollagen:native collagen=1:5). For the confirmation of these results, subsequent experiments were performed.

3-2. Measurement of MMP Expression According to Collagen Types

Since dermal contraction is generally associated with expression of MMPs, the expression levels of MMP-2 and MMP-9 in culture medium, where the three-dimensionally cultured skin tissues of Experimental Groups 1 to 3 were prepared in Example 3-1 according to collagen types, were analyzed. The expression level of each MMP was quantitatively analyzed by ELISA.

As a result, as can be confirmed in FIG. 5, it was confirmed that the expression levels of MMP-2 and MMP-9 in Experimental Group 1 (in which the dermis was prepared by using atelocollagen only) were significantly higher (at least two times) compared to those in Experimental Group 2 (in which the dermis was prepared by using native collagen only) and Group 3. In contrast, the expression levels of MMP-2 and MMP-9 in Experimental Group 3 (in which the dermis was prepared by mixing atelocollagen with native collagen) were similar to those in a case where the dermis was prepared by using native collagen only.

These results suggest that the variations in dermal contraction according to collagen types can occur not only by the simple difference in collagen degradation but also by altering the level of MMP expression. This was the first demonstration by the present inventors that such a difference can occur even by adding a small amount of native collagen.

3-3. Preparation of a Three-Dimensionally Cultured Skin Model According to the Collagen Mixing Ratio Three-dimensionally cultured skin models were prepared by varying the mixing ratios between atelocollagen and native collagen. Specifically, the models were prepared in Experimental Group A (where atelocollagen and native collagen were mixed at a 1:1 ratio), Experimental Group B (where atelocollagen and native collagen were mixed at a 1:5 ratio), and Experimental Group C (where atelocollagen and native collagen were mixed at a 1:10 ratio).

As a result, as can be confirmed in FIG. 6, it was confirmed that epidermis and dermis were stably constituted at a 1:1 ratio in all Experimental Groups. No collagen contraction was observed. Accordingly, it was confirmed that three-dimensionally cultured skin models are stably prepared without dermal contraction in the range of 1:1 to 1:10.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

---

What is claimed is:

1. A method for preparing a three-dimensionally cultured skin model comprising dermis and epidermis, comprising:
    (a) inoculating a composition, which comprises murine fibroblasts or human fibroblasts; and a combination of native collagen and atelocollagen, into a culture dish and solidifying the same to prepare the dermis, wherein atelocollagen and native collagen are combined in a ratio of 1:1 to 1:10;
    (b) inoculating keratinocytes on the dermis prepared in step (a) and culturing until a cell sheet is formed thereon; and
    (c) raising the cell sheet in step (b) to the air/liquid interface to form the upper layers of epidermis, thereby preparing said three-dimensionally cultured skin model comprising dermis and epidermis, wherein said dermis formed in step (a) by a combination of native collagen and atelocollagen exhibits at least one of the following characteristics compared to when atelocollagen is used alone:
    i) inhibition of dermal contraction,
    ii) increase in epidermal differentiation;
    iii) decrease in the level of MMP expression; and
    iv) inhibition of collagen degradation.

2. The method of claim 1, wherein, in step (a),
    the native collagen comprises alpha-1 chain consisting of the amino acid sequence of SEQ ID NO: 1 and alpha-2 chain consisting of the amino acid sequence of SEQ ID NO: 2; and
    the atelocollagen comprises alpha-1 chain consisting of the amino acid sequence of SEQ ID NO: 3 and alpha-2 chain consisting of the amino acid sequence of SEQ ID NO: 4.

3. The method of claim 1, wherein, in step (a), the composition, which comprises murine fibroblasts or human fibroblasts; and a combination of native collagen and atelocollagen, comprises $1 \times 10^4$ to $1 \times 10^7$ murine fibroblasts or human fibroblasts per cm$^2$.

4. The method of claim 1, wherein, in step (a), the composition further comprises at least one cell selected from the group consisting of fibroblasts, dermal papilla cells, endothelial cells, adipocytes, and mesenchymal stem cells.

5. The method of claim 1, wherein step (a) is performed for 1 hour to 48 hours.

6. The method of claim 1, wherein $1 \times 10^4$ to $1 \times 10^7$ keratinocytes per cm$^2$ of the dermis prepared in step (a) are inoculated in step (b).

7. The method of claim 1, wherein the keratinocytes in step (b) are derived from the skin, mucosa, cornea, or hair follicles.

8. The method of claim 1, wherein step (b) further comprises inoculating at least one cell selected from the group consisting of melanocytes, Merkel cells, and Langerhans cells.

9. The method of claim 1, wherein step (c) is performed for 7 days to 21 days.

10. A three-dimensionally cultured skin model prepared by the method of claim 1.

* * * * *